United States Patent [19]

Snoke

[11] Patent Number: 5,857,996
[45] Date of Patent: *Jan. 12, 1999

[54] METHOD OF EPIDERMAL SURGERY

[75] Inventor: Phillip Jack Snoke, Atlanta, Ga.

[73] Assignee: Catheter Imaging Systems, Atlanta, Ga.

[*] Notice: The term of this patent shall not extend beyond the expiration date of Pat. No. 5,354,266.

[21] Appl. No.: 957,998

[22] Filed: Oct. 22, 1997

Related U.S. Application Data

[63] Continuation of Ser. No. 606,084, Feb. 23, 1996, abandoned, which is a continuation of Ser. No. 321,174, Oct. 11, 1994, Pat. No. 5,496,269, which is a continuation of Ser. No. 129,331, Sep. 30, 1993, Pat. No. 5,354,266, which is a continuation-in-part of Ser. No. 908,403, Jul. 6, 1992, Pat. No. 5,342,299, Ser. No. 963,431, Oct. 19, 1992, Pat. No. 5,423,311, and Ser. No. 970,490, Nov. 2, 1992, Pat. No. 5,399,164.

[51] Int. Cl.$^6$ .................................................. A61M 1/00
[52] U.S. Cl. ............................... 604/28; 604/54; 128/898
[58] Field of Search ............................... 604/28, 48, 49, 604/51, 53, 54, 95; 128/898

[56] References Cited

U.S. PATENT DOCUMENTS

| | | |
|---|---|---|
| Re. 33,854 | 3/1992 | Adair . |
| D. 202,552 | 10/1965 | Rose . |
| D. 243,115 | 1/1977 | Ziegler et al. . |
| D. 286,280 | 10/1986 | Holtman et al. . |
| D. 310,721 | 9/1990 | Beisang, III . |
| D. 338,958 | 8/1993 | Jensen . |
| D. 343,678 | 1/1994 | Snoke et al. . |
| D. 347,473 | 5/1994 | Nitzsche . |
| D. 349,340 | 8/1994 | Snoke et al. . |
| D. 350,605 | 9/1994 | Williams . |
| D. 351,652 | 10/1994 | Thompson et al. . |
| D. 359,801 | 6/1995 | Boykin . |
| D. 382,959 | 8/1997 | Arpe . |

(List continued on next page.)

FOREIGN PATENT DOCUMENTS

| | | |
|---|---|---|
| 0 343 094 | 1/1989 | European Pat. Off. . |
| 0 343 094 A2 | 1/1989 | European Pat. Off. . |
| 0 370 158 | 5/1990 | European Pat. Off. . |
| 0389453 | 9/1990 | European Pat. Off. . |
| 0 489 937 | 6/1992 | European Pat. Off. . |
| 489937 | 6/1992 | European Pat. Off. . |
| 990417 | 9/1951 | France . |
| 2655548 | 6/1991 | France . |

(List continued on next page.)

OTHER PUBLICATIONS

AngioLaz Ultra–Vu™, Angiolaz Epidural Ultra–Vu Scope.
*Anesthesiology* Pain Management in the 21$^{st}$ Century: An Anesthesiologist's Look into the Crystal Ball, Steven D. Waldman, M.D.
Eighteen–Gauge Microscopic–Telescopic Needle Endoscope with Electrode Channel: Potential Clinical and Research Application, Charles P. Olinger, M.D. and R. L. Ohlhaber, *Surg. Neuol.* vol. 2, May 1974.
"The Dorsomedian Connective Tissue Band in the Lumbar Epidural Space of Humans: An Anatomical Study Using Epiduroscopy in Autopsy Cases" Rune Blomberg, M.D. 1986 by the International Anesthesia Research Society.

(List continued on next page.)

*Primary Examiner*—Ronald Stright, Jr.
*Assistant Examiner*—A. T Nguyen
*Attorney, Agent, or Firm*—Allen, Dyer, Doppelt, Milbrath & Gilchrist

[57] ABSTRACT

A method of epidural surgery is provided that improves visibility in the epidural space of a patient for more effectively conducting therapeutic surgery therein. The method includes the steps of distending a portion of the epidural space of a patient by filling the portion of the epidural space with a fluid supplied from a catheter and positioning a portion of an optical scope in the distended portion of the epidural space by inserting the optical scope through the same catheter that supplies the distending fluid to thereby provide a visual image of the epidural space.

2 Claims, 8 Drawing Sheets

5,857,996
Page 2

U.S. PATENT DOCUMENTS

| | | |
|---|---|---|
| D. 384,746 | 10/1997 | Varn . |
| 922,985 | 10/1909 | Wappler . |
| 3,470,876 | 10/1969 | Barchiton . |
| 3,500,820 | 3/1970 | Almen . |
| 3,605,725 | 9/1971 | Bentov . |
| 3,625,200 | 12/1971 | Muller . |
| 3,773,034 | 11/1973 | Burns et al. . |
| 3,788,304 | 1/1974 | Takahashi . |
| 3,831,017 | 8/1974 | Auer . |
| 3,892,228 | 7/1975 | Mitsui . |
| 3,948,251 | 4/1976 | Hosono . |
| 4,273,111 | 6/1981 | Tsukaya . |
| 4,279,245 | 7/1981 | Takagi et al. . |
| 4,327,723 | 5/1982 | Frankhouser . |
| 4,344,092 | 8/1982 | Miller . |
| 4,353,358 | 10/1982 | Emerson . |
| 4,390,012 | 6/1983 | Mizumoto . |
| 4,413,278 | 11/1983 | Feinbloom . |
| 4,417,886 | 11/1983 | Frankhouser et al. . |
| 4,421,106 | 12/1983 | Uehara . |
| 4,433,675 | 2/1984 | Konoshima . |
| 4,475,539 | 10/1984 | Konomura . |
| 4,483,326 | 11/1984 | Yamaka et al. . |
| 4,515,592 | 5/1985 | Frankhouser . |
| 4,539,586 | 9/1985 | Danna et al. . |
| 4,543,090 | 9/1985 | McCoy . |
| 4,545,374 | 10/1985 | Jacobson . |
| 4,573,448 | 3/1986 | Kambin . |
| 4,577,621 | 3/1986 | Patel . |
| 4,580,551 | 4/1986 | Siegmund et al. . |
| 4,587,972 | 5/1986 | Morantte, Jr. . |
| 4,589,404 | 5/1986 | Barath et al. . |
| 4,590,923 | 5/1986 | Watanabe . |
| 4,601,284 | 7/1986 | Arakawa et al. . |
| 4,611,888 | 9/1986 | Prenovitz et al. . |
| 4,625,713 | 12/1986 | Hiraoka . |
| 4,644,960 | 2/1987 | Johans . |
| 4,649,904 | 3/1987 | Krauter et al. . |
| 4,651,202 | 3/1987 | Arakawa . |
| 4,653,476 | 3/1987 | Bonnet . |
| 4,713,057 | 12/1987 | Huttner et al. . |
| 4,737,142 | 4/1988 | Heckele . |
| 4,745,908 | 5/1988 | Wardie . |
| 4,748,969 | 6/1988 | Wardie . |
| 4,750,475 | 6/1988 | Yoshihashi . |
| 4,753,222 | 6/1988 | Morishita . |
| 4,758,222 | 7/1988 | McCoy . |
| 4,776,844 | 10/1988 | Ueda . |
| 4,782,819 | 11/1988 | Adair . |
| 4,791,912 | 12/1988 | Tashiro . |
| 4,793,326 | 12/1988 | Shishido . |
| 4,797,737 | 1/1989 | Yazawa . |
| 4,799,496 | 1/1989 | Hargreaves et al. . |
| 4,808,157 | 2/1989 | Coomba . |
| 4,815,450 | 3/1989 | Patel . |
| 4,834,710 | 5/1989 | Fleck . |
| 4,844,053 | 7/1989 | Dittrich . |
| 4,853,773 | 8/1989 | Hibino et al. . |
| 4,867,529 | 9/1989 | Utsumi et al. . |
| 4,884,133 | 11/1989 | Kanno et al. . |
| 4,890,602 | 1/1990 | Hake . |
| 4,893,613 | 1/1990 | Hake . |
| 4,901,142 | 2/1990 | Ikuno et al. . |
| 4,904,237 | 2/1990 | Janese . |
| 4,905,666 | 3/1990 | Fukuda . |
| 4,906,230 | 3/1990 | Maloney et al. . |
| 4,911,148 | 3/1990 | Sosnowski et al. . |
| 4,919,112 | 4/1990 | Siegmund . |
| 4,919,653 | 4/1990 | Martinez et al. . |
| 4,920,413 | 4/1990 | Nakamura et al. . |
| 4,924,856 | 5/1990 | Noguchi . |
| 4,930,521 | 6/1990 | Metzger et al. . |
| 4,933,816 | 6/1990 | Hug et al. . |
| 4,934,340 | 6/1990 | Ebling et al. . |
| 4,954,129 | 9/1990 | Giuliani et al. . |
| 4,968,295 | 11/1990 | Neumann . |
| 4,968,298 | 11/1990 | Michelson . |
| 4,972,828 | 11/1990 | Ito . |
| 4,973,312 | 11/1990 | Andrew . |
| 4,973,329 | 11/1990 | Park et al. . |
| 4,979,496 | 12/1990 | Komi . |
| 4,983,165 | 1/1991 | Loiterman . |
| 4,986,258 | 1/1991 | Cho et al. . |
| 4,989,582 | 2/1991 | Sakiyama et al. . |
| 4,996,974 | 3/1991 | Ciarlei . |
| 5,004,456 | 4/1991 | Botterbusch et al. . |
| 5,010,875 | 4/1991 | Kato . |
| 5,024,655 | 6/1991 | Freeman et al. . |
| 5,042,915 | 8/1991 | Akutsu et al. . |
| 5,053,046 | 10/1991 | Janese . |
| 5,058,568 | 10/1991 | Irion et al. . |
| 5,084,043 | 1/1992 | Hertzman et al. . |
| 5,085,631 | 2/1992 | Leighton . |
| 5,090,959 | 2/1992 | Samson et al. . |
| 5,101,807 | 4/1992 | Kawashima . |
| 5,125,906 | 6/1992 | Fleck . |
| 5,131,382 | 7/1992 | Meyer . |
| 5,134,469 | 7/1992 | Uchimura . |
| 5,143,475 | 9/1992 | Chikama . |
| 5,151,096 | 9/1992 | Khoury . |
| 5,167,221 | 12/1992 | Chikama . |
| 5,188,594 | 2/1993 | Zilberstein . |
| 5,195,541 | 3/1993 | Obenchain . |
| 5,197,649 | 3/1993 | Bessler et al. . |
| 5,199,417 | 4/1993 | Muller et al. . |
| 5,199,950 | 4/1993 | Schmitt . |
| 5,215,105 | 6/1993 | Kizelshteyn et al. . |
| 5,217,454 | 6/1993 | Khoury . |
| 5,232,442 | 8/1993 | Johnson et al. . |
| 5,267,573 | 12/1993 | Evans et al. . |
| 5,273,535 | 12/1993 | Edwards et al. . |
| 5,275,151 | 1/1994 | Shockey et al. . |
| 5,328,467 | 7/1994 | Edwards et al. . |
| 5,342,299 | 8/1994 | Snoke et al. . |
| 5,344,397 | 9/1994 | Heaven et al. . |
| 5,354,266 | 10/1994 | Snoke . |
| 5,396,880 | 3/1995 | Kagan et al. . |
| 5,399,164 | 3/1995 | Snoke et al. . |
| 5,415,158 | 5/1995 | Barthel et al. . |
| 5,423,311 | 6/1995 | Snoke et al. . |
| 5,437,636 | 8/1995 | Snoke et al. . |
| 5,526,820 | 6/1996 | Khoury . |
| 5,531,687 | 7/1996 | Snoke et al. . |
| B1 4,539,586 | 12/1991 | Danna et al. . |

FOREIGN PATENT DOCUMENTS

| | | |
|---|---|---|
| 1213571 | 3/1966 | Germany . |
| 39116288 | 11/1989 | Germany . |
| 3916288 A1 | 11/1989 | Germany . |
| WO 88/00810 | 2/1988 | WIPO . |
| WO88/00810 | 2/1988 | WIPO . |
| WO91 01772 | 2/1991 | WIPO . |
| WO 91/11213 | 8/1991 | WIPO . |
| WO91/11213 | 8/1991 | WIPO . |
| WO93/15648 | 8/1993 | WIPO . |
| WO94/27666 | 12/1994 | WIPO . |

OTHER PUBLICATIONS

Physiology, Pathophysiology and Pharmacology of Local Anaethetics Used in Regional Anaesthesia, presented by B. G. Covino and G. T. Tucker.

Hogan, Quinn H., M.D., "Lumbar Epidural Anatomy", *Anesthesiology*, vol. 75, pp. 767–775 (1991).

Pick et al., "Endoscopic Examinations and Computed Tomography Concerning Cervical Spine Positioning in Treatment of Acute Cervical Spine Injuries", *Archives of Orthopaedic and Traumatic Surgery*, vol. 97, pp. 43–49 (1980).

Pool, Lawrence J., "Direct Visualation of Dorsal Nerve Roots of the Cauda Equina by Means of Myeloscpe", *Archives of Neurology and Psychiatry*, pp. 1308–1312.

Harrison et al., "Resin Injection Studies of the Extradural Space", *British Journal of Anaesthesia*, vol. 57, pp. 333–336 (1985).

Blomberg, R., "A Method for Epiduroscopy and Spinaloscopy", *Acta Anaesthesiology Scand*, vol. 29, pp. 113–116 (1985).

Ooi et al., "Myeloscopy, with Special Reference to Blood Flow Changes in the Cauda Equina During Lasègue's Test", *Int'l Orthopaedics (SICOT)*, vol. 4, pp. 307–311 (1981).

Shimoji et al., "Observation of Spinal Canal and Cisternae with the Newly Developed Small–diameter, Flexible Fiberscopes", *Anesthesiology*, vol. 75, pp. 341–344 (1991).

Blomberg et al., "The Lumbar Epidural Space in Patients Examined with Epiduroscopy", *Aneth Analg*, vol. 68, pp. 157–160 (1989).

Stern, Lincoln E., "The Spinascope: A New Instrument for Visualizing the Spinal Canal and Its Contents", *Medical Record*, pp. 31–32 (1936).

Ooi et al., "Myeloscopy", *Int'l Orthopaedics (SICOT)*, vol. 1, pp. 107–111 (1977).

Burman, Michael S., "The Direct Visualization of the Spinal Canal and Its Contents", pp. 695–696.

Pool, Lawrence J., "Myeloscopy: Intraspinal Endoscop," *Surgery*, vol. 11, pp. 169–182 (Feb. 1942).

Shimoji et al., "Observation of Spinal Canal and Cisternae with the Newly Developed Small–diameter, Flexible Fiberscopes," *Anesthesiology*, vol. 75, pp. 341–344, (1991).

Waldman, Steven D., "Pain Management in the 21st Century: An Anesthesiologist's Look Into the Crystal Ball," *American Journal of Pain Management*, vol. 1 (Oct. 1991).

Hillmer, Michael, "Back Talk," *Spirit*, p. 32 (Oct. 1991).

Springer, Ilene, "Back Talk," pp. 114, 118, 122.

Shantha 3et al., "Subdural Blood Patch for Spinal Headache," *The New England Journal of Medicine*, vol. 325, No. 17, pp. 1252–1253 (Oct. 1991).

*Caudal Analgesia*, pp. 264–265.

"Actual Position of Spinal and Epidural Anaesthesia," pp. 42–43.

"Insertion of the Catheter," *Continuous Epidual Analgesia*, pp. 218–223.

"Sacral Epidual (Caudal) Block," *Principles and Practice of Regional Anaesthesia*, pp. 105–106, 108.

"Spinal Analgesia," *Anatomy*, p. 61.

Fortuna, Armando, "Caudal Epidual Anethesia in Latin–America," p. 928.

Bromage, *Drugs and Equipment*, pp. 333–334.

Blomberg et al., "The Lumbar Epidural Space in Patients Examined with Epiduroscopy," *Anesth. Analg.*, vol. 68, pp. 157–160 (1989).

Hogan et al., "Epidual Steroids and the Outcomes Movement," Pain Digest, vol. 1, pp. 269–270 (1992).

"Epidural Endoscopy Excerpts and Comments" Yale University School of Medicine, Center for Pain Management:; Apr. 1992.

"Exploring Epidural Endoscopy" Diagnostic Images Using the Ultra–Vu™ Scopy in Pain Management Applications; Apr. 1992.

"Exploring Epidural Endoscopy" Diagnostic Imnages Using the Ultra–Vu™ Scopy: Apr. 1992.

"Experimental Procedures at Yale University by Dr. Randy Rizor," Apr. 16, 1992—Tape 1 of 3.

Experimental Procedures at Yale University by Dr. Randy Rizor, Apr. 6, 1992—Tape 2 of 3.

"Experimental Procedures at Yale University by Dr. Randy Rizor," Apr. 16, 1992—Tape 3 of 3.

Seldinger, Sven I., "Catheter Replacement of the Needle in Percutaneous Arteriography," *American Journal of Roentgenology*, vol. 142, pp. 5–7 (1984).

Declaration of Dr. Dennis W. Coombs dated Sep. 19, 1996 in Myelotec, Inc. and Edward J. Lortie, Jr., v. Catheter Imaging Systems, Inc. pp. 1–4.

Declaration of Dr. Yasin Kahn in Myelotec, Inc. and Edward J. Lortie, Jr., v. Catheter Imaging Systems, Inc., pp. 1–2.Myelotec, Inc. and Edward J. Lortie, Jr., v. Catheter Imaging Systems, Inc.

Declaration of Dr. Luke M. Kitahata dated Nov. 1 Myelotec, Inc. and Edward J. Lortie, Jr., v. Catheter Imaging Systems, Inc., pp. 1–3.

Declaration of Ronald G. Seifert dated Nov. 18, 1996 in Myelotec, Inc. and Edward J. Lortie, Jr., v. Catheter Imaging, Inc., pp. 1–2.

Affidavit of Thomas R. Long executed Nov. 11, 1996 in Myelotec, Inc., and Edward J. Lortie, Jr., v. Catheter Imaging Systems, Inc., pp. 1–17.

Deposition of Jack Snoke, dated 24 Oct. 1996, in Myelotec, Inc. and Edward J. Lortie Jr., v. Catheter Imaging Systems, Inc., pp. 1–11.

Affidavit of Geoffrey Harrison Galley executed Sep. 7, 1994 pp. 1–7.

Affidavit of Vernon Milton Levey executed Sep. 7, 1994 pp. 1–2.

Affidavit of Paul Z. Lundbergh dated Sep. 12, 1996 in Myelotec, Inc. and Edward J. Lortie, Jr., v. Catheter Imaging Systems, Inc., (3 pages and attached Exhibits A and B).

Affidavit of Hurley J. Blakeney dated Oct. 6, 1996, in Myelotec, Inc. and Edward J. Lortie, Jr., v. Catheter Imaging Systems, Inc., pp. 1–7.

Affidavit of Allen Elphick executed Nov. 11, 1996 in Myelotec, Inc. and Edward J. Lortie, Jr., v. Catheter Imaging Systems, Inc., pp. 1–3.

Affidavit of David Clatworthy executed Nov. 6, 1996 in Myelotec, Inc. and Edward J. Lortie, Jr., v. Catheter Imaging Systems, Inc., pp. 1–7.

Angio Laz Ultra–Vu™ brochure, pp. 1–3.

Deposition of Adib Issaac Khoury dated Oct. 10, 1996 Condensed Transcript and Concordance in Myelotec, Inc. and Edward J. Lortie, Jr., v. Catheter Imaging Systems, Inc., pp. 1–17.

Deposition of P. Jack Snoke Oct. 24, 1996 in Myelotec, Inc. and Edward J. Lortie, Jr., v. Catheter Imaging Systems, Inc., pp. 1–99.

Exhibits 1–13 to Deposition of P. Jack Snoke Oct. 24, 1996 in Myelotec, Inc. and Edward J. Lortie, Jr., v. Catheter Imaging Systems, Inc., pp. 1–68.

Videotape Depostion of Lloyd Saberski, M.D., Nov. 7, 1996, in Myelotec, Inc. and Edward J. Lortie, Jr., v. Catheter Imaging Systems, Inc., pp. 1–118.

Deposition of Ron Luther, Nov. 6, 1996, Condensed Transcript and Concordance in Myelotec, Inc. and Edward J. Lortie, Jr., v. Catheter Imaging Systems, Inc., pp. 1–9.

Cirriculm Vitae of Neil Kahanovitz, M.D. pp. 1–31.

Deposition of Neil Kahanovitz, M.D. Nov. 15, 1996, Condensed Transcript and Concordance in Myelotec, Inc. and Edward J. Lortie, Jr., v. Catheter Imaging Systems, Inc., pp. 1–9.

Deposition of Dan Page, Nov. 15, 1996. Condensed Transcript and Concordance in Myelotec, Inc. and Edward J. Lortie, Jr., v. Catheter Imaging Systems, Inc., pp. 1–7.

Deposition of Edward J. Lortie, Jun. 30, 1994 in Catheter Imaging Systems, Inc., v. Edward J. Lortie, Jr., Civil Action E23514, pp. 1–129.

Deposition of Edward J. Lortie, Jun. 30, 1994 in Myelotec, Inc. and Edward J. Lortie, Jr., v. Catheter Imaging Systems, Inc., pp. 1–153.

"Dynspace Systems, Inc. Introduces The New England Epidural Ultra VU* Scope System" from ASA Mee4ting San Francisco, CA Oct. 28–31, 1991 pp. 1–4.

"Epidual Endoscopy Excerpts and Comments" Yale University School of Medicine, Center for Pain Managment; Apr. 1992.

"Exploring Epidural Endoscopy" The Ultra–Vu™ Scope in Pain Management Application Experimental Procedures at Yale University by Dr. Randy Rizor, Apr. 6, 1992—Tape 1 of 3 ons; Apr. 1992.

"Experimental Procedures at Yale University by Dr. Randy Rizor," Apr. 6, 1992—Tape 1 of 3.

"Experimental Procedures at Yale University by Dr. Randy Rizor," Apr. 6, 1992—Tape 2 of 3.

"Experimental Procedures at Yale University by Dr. Randy Rizor," Apr. 6, 1992—Tape 3 of 3.

Affidavit of Randy Frank Rizor, M.D. executed Sep. 20, 1996 in Myelotec, Inc. and Edward J. Lortie, Jr., v. Catheter Imaging Systems, Inc., pp. 1–5.

Second Affidavit of Randy Frank Rizor, M.D. dated Nov. 13, 1996.

Catheter Imaging Systems, Inc. v. Myelotec, Inc. and Edward J. Lortie, Jr., Civil Action 1–97–CV–0025 Notice of Petitioner's Motion to Confirm Arbitration Award filed in U. S. Patents 5,354,266 and 5,496,269.

"Epidural Endoscopy Execpts and Comments" Yale University School of Medicine, Center for Pain Management; Apr. 1992.

"Exploring Epidural Endoscopy" The Ultra–Vu™ Scope in Pain Management Applications; Apr. 1992.

"Exploring Epidural Endoscopy" Diagnostic Images Using the Ultra–Vu™ Scope; Apr. 1992.

"Experimental Procedures at Yale University by Dr. Randy Rizor", Apr. 6, 1992—Tape 1 of 3.

"Experimental Procedures at Yale University by Dr. Randy Rizor", Apr. 6, 1992—Tape 2 of 3.

"Experimental Procedures at Yale University by Dr. Randy Rizor", Apr. 6, 1992—Tape 3 of 3.

"Notice of Arbitration Award" Pursuit to 37 CFR 1.335 and 35 U.S.C. § 294 In re U.S. Patent of: Phillip Jack Snoke Serial No.: 08/321,174—Patent No.: 5,496,269 For: Method of Epidural Surgery.

"Notice of Arbitration Award" pursuant to 37 CFR 1.3335 and 35 U.S.C. § 294 In re U.S. Patent of: Phillip Jack Snoke Serial No.: 08/129,331—Patent No.: 5,354,266 For: Method of Epidural Surgery.

Seldinger, Sven I., "Catheter Replacement of the Needle in Percutaneous Arteriography", *American Journal of Roentgenology*, vol. 142, pp. 5–7 (1984).

Shimoji et al., "Observation of Spinal Canal and Cisternae with the Newly Developed Small–diameter, Flexible Fiberscopes", *Anesthesiology*, vol. 75, pp. 341–344, (1991).

Waldman, Steven D., "Pain Management in the 21st Century: An Anesthesiologist's Look Into the Crystal Ball", *American Journal of Pain Management*, vol. 1 (Oct. 1991).

Hillmer, Michael, "Back Talk", *Spirit*, p. 32 (Sep. 1991).

Springer, Ilene, "Back Talk", pp. 114, 118, 122.

Shantha et al., "Subdural Blood Patch for Spinal Headache", *The New England Journal of Medicine*, vol. 325, No. 17, pp. 1252–1253 (Sep. 1991).

*Caudal Analgesia*, pp. 264–265.

"Actual Position of Spinal and Epidural Anaesthesia", pp. 42–43.

"Sacral Epidural (Caudal) Block", *Principles and Practice of Regional Anaesthesia*, pp. 105–106, 108.

Fortuna, Armando, "Caudal Epidural Anesthesia in Latin–America", p. 928.

Bromage, *Drugs and Equipment*, pp. 333–334.

Blomberg et al., "The Lumbar Epidural Space in Patients Examined with Epiduroscopy", *Anesth Analq*, vol. 68, pp. 157–160 (1989).

Hogan et al., "Epidural Steroids and the Outcomes Movement", *Pain Digest*, vol. 1, pp. 269–270 (1992).

Hogan, Quinn H., M.D., "Lumbar Epidural Anatomy", *Anesthesiology*, vol. 75, pp. 767–775 (1991).

Pool, Lawrence J., "Direct Visualization of Dorsal Nerve Roots of the Cauda Equina by Means of Myeloscope", *Archives of Neurology and Psychiatry*, pp. 1308–1312.

Harrison et al., "Resin Injection Studies of the Lumbar Extradural Space", *British Journal of Anaesthesia*, vol. 57, pp. 333–336 (1985).

Blomberg, R., "A Method for Epiduroscopy and Spinaloscopy", *Acta Anaesthesiology Scand*, vol. 29, pp. 113–116 (1985).

Ooi et al., "Myeloscopy, with Special Reference to Blood Flow Changes in the Cauda Equina During Lasegue's Test", *Int'l Orthopaedics (SICOT)*, vol. 4, pp. 307–311 (1981).

Shimoji et al., "Observation of Spinal Canal and Cisternae with the Newly Developed Small–diameter, Flexible Fiberscopes", *Anesthesiology*, vol. 75, pp. 341–344 (1991).

Blomberg et al., "The Lumbar Epidural Space in Patients Examined with Epiduroscopy", *aneth Analg*, vol. 68, pp. 157–160 (1989).

Stern, Lincoln E., "The Spinascope: A New Instrument for Visualizing the Spinal Canal and Its Contents", *Medical Record*, pp. 31–32 (1936).

Ooi et al., "Myeloscopy", *Int'l Orthopaedics (SICOT)*, vol. 1, pp. 107–111 (1977).

Burman, Michael S., "The Direct Visualization of the Spinal Canal and Its Contents", pp. 695–696.

Pool, Lawrence J., "Myeloscopy: Intraspinal Endoscopy", *Surgery*, vol. 11, pp. 169–182 (Feb. 1942).

METHOD OF EPIDERMAL SURGERY

RELATED APPLICATIONS

This application is a continuation of Ser. No. 08/606,084 filed Feb. 23, 1996, which is a continuation of Ser. No. 08/321,174, filed Oct. 11, 1994 now U.S. Pat. No. 5,496,269, which is a continuation of Ser. No. 08/129,331, filed Sep. 30, 1993, now U.S. Pat No. 5,354,266, which is a continuation-in-part of U.S. patent applications Ser. No. 07/908,403 filed on Jul. 6, 1992, now U.S. Pat No. 5,342,299, Ser. No. 07/963,431 filed on Oct. 19, 1992, now U.S. Pat No. 5,423,311 and Ser. No. 07/970,490 filed on Nov. 2, 1992, now U.S. Pat. No. 5,399,164.

FIELD OF THE INVENTION

This invention relates to surgical methods, and more particularly to methods of epidural surgery in and around the epidural space.

BACKGROUND OF THE INVENTION

Back pain, and particularly lower back pain, is a major expense to society and is one of the most common disabling problems of those of working age. Injuries to the back vary from herniated disks of the spine to muscle strains and nerve damage. In the back or posterior end of the human body, the epidural space is potential space located in and extending the length of the spine. The epidural space is defined along one edge or side by the dura mater which surrounds the spinal cord. The epidural space is further defined along a second edge or side by the periosteum of the bony vertebrae or by the ligamentum-flavum at the vertebral interspaces. Along the interior surface of the ligamentum-flavum lies the venus plexus, a complex configuration of veins. The epidural space contains fat, connective tissue, blood vessels, lymphatic vessels, nerve fibers, and other structures. Various lesions, cystical masses, and nerve damage can occur in and around the epidural space which causes various back problems for the human body.

Although applying anesthesia to the epidural space has been known for procedures such as child birth or the like, the anatomy of the epidural space and related structures has not been fully investigated. Conventionally, the insertion of a catheter, fluid introducer, or the like for inducing spinal anesthesia directly into the subarachnoid space of the spinal column, such as seen in U.S. Pat. No 5,232,442 by Johnson, et al. entitled *"Method And Apparatus For Inducing Anesthesia"*, has been through fluoroscopic or radiographic observation. Fluoroscopic observation techniques have also been used to try to locate the various sources of problems associated with back pain such as seen in U.S. Pat. No. 5,215,105 by Kizelshteyn, et al. entitled *"Method Of Treating Epidural Lesions"*. The fluoroscopic techniques are helpful for general guidance of instruments or other devices, but fail to give the physician or other medical personnel a detailed picture of structures within vessels or cavities, such as the epidural space, and therefore are limited in identifying the source of back pain problems.

Also, endoscopes have been used whereby internal areas or organs within a body vessel or cavity may be observed by inserting an elongated insertable part of the endoscope through a tube or sleeve inserted into a body vessel or cavity, or directly into the body vessel or cavity itself, such as seen in U.S. Pat. No. 5,195,541 by Obenchain entitled *"Method Of Performing Laparoscopic Lumbar Discectomy"*. An endoscope, as used herein, is an instrument for examining the interior of a bodily canal or hollow organ. A catheter, on the other hand, is a tube inserted into a bodily channel, such as a vein, to maintain an opening to a body vessel or cavity. These endoscopes, however, are relatively large with respect to a catheter and, therefore, do not cooperate with a catheter for performing delicate surgery such as the type surrounding the back or spinal column.

Further, fiber optic scopes or fiberscopes have been used for various types of surgery such as surrounding the heart. These fiberscopes often are inserted into a vein or an artery for viewing blockage or the like within the vein or artery. The epidural space, however, has not fully been explored using visual techniques because the epidural space, as described above, does not take the form of a vein or artery. Because the epidural space collapses around an instrument or device inserted therein such as a catheter, an endoscope, a fiberscope, or a cutting tool, the space has not been considered for optical scope viewing or for performing many types of epidural surgical procedures.

Therefore, there is still a need for a method of epidural surgery that allows a physician to effectively enter the epidural space of a patient, visually observe and document a problem area which could be the source of back pain in the patient, and therapeutically treat the problem area in or around the epidural space in a minimal amount of time and with minimal amount of cutting and other potential damage to the patient during surgery.

SUMMARY OF THE INVENTION

The present invention provides a method of epidural surgery that improves visibility in the epidural space of a patient for more effectively conducting therapeutic surgery therein. The method of epidural surgery involves distending a portion of the epidural space by filling the portion of the epidural space with a fluid supplied from a catheter positioned in the epidural space and positioning a portion of an optical scope in the distended portion of the epidural space by inserting the optical scope through the catheter to thereby provide a visual image of the epidural space. The method of epidural surgery also allows a physician, or other medical personnel, to control and manipulate the catheter and an imaging source while simultaneously using surgical tools, such as fiberoptic scopes or the like, and fluids needed for medical operations to thereby allow the physician to positionally locate, isolate, and view problem areas within the epidural space. Because the method of epidural surgery minimizes cutting and other potential damage to the patient during surgery, the invention provides a method of epidural surgery that often can be performed as an outpatient procedure.

BRIEF DESCRIPTION OF THE DRAWINGS

Some of the objects and advantages of the present invention having been stated, others will become apparent as the description proceeds when taken in conjunction with the accompanying drawings, in which.

DESCRIPTION OF ILLUSTRATED EMBODIMENTS

The present invention now will be described more fully hereinafter with reference to the accompanying drawings in which a preferred embodiment of the invention is shown. Like numbers refer to like elements throughout.

Figure 1:
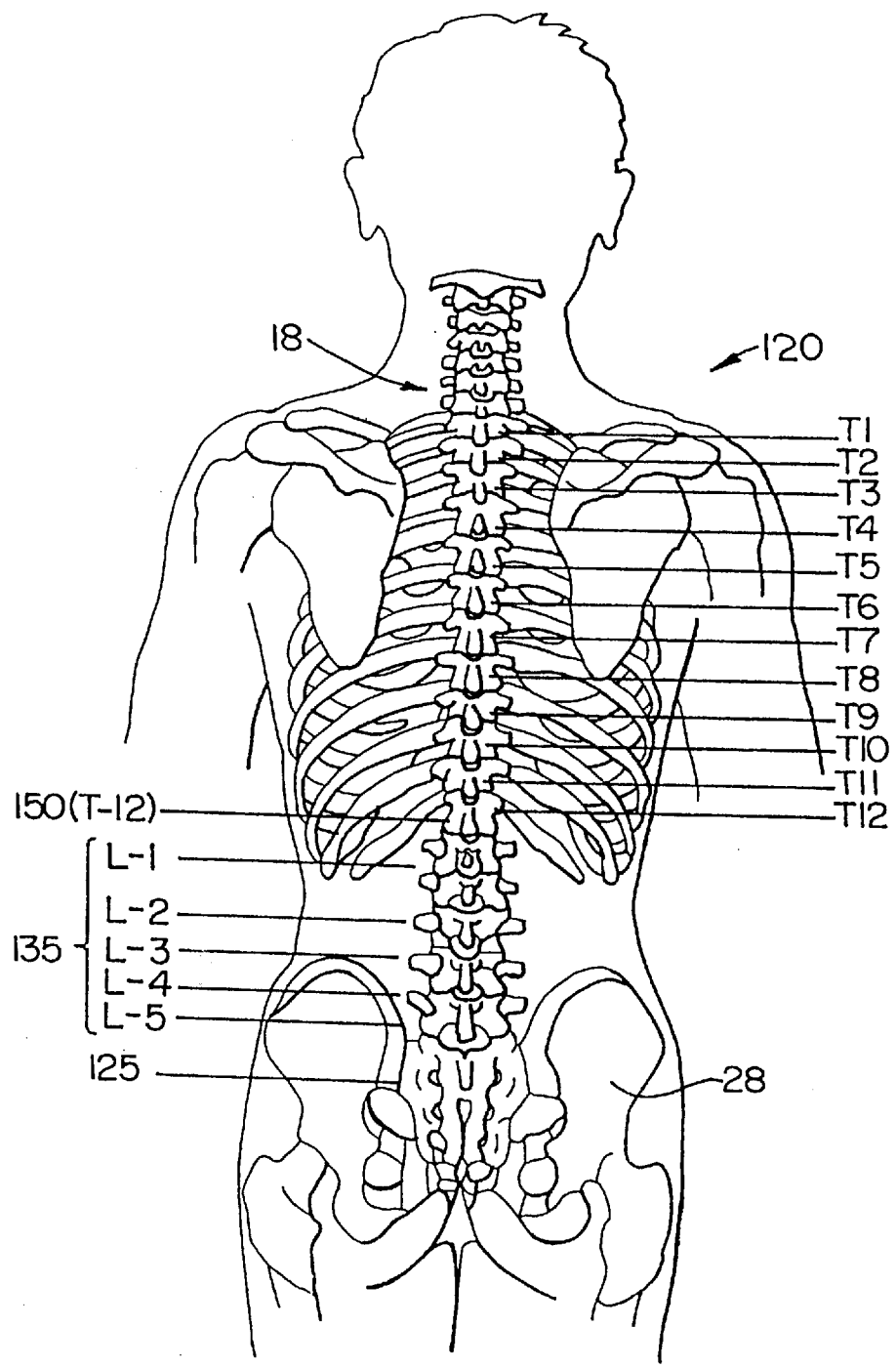
FIG. 1 is a fragmentary skeletal view of a human body illustrating spinal column regions thereof.
Figure 2:
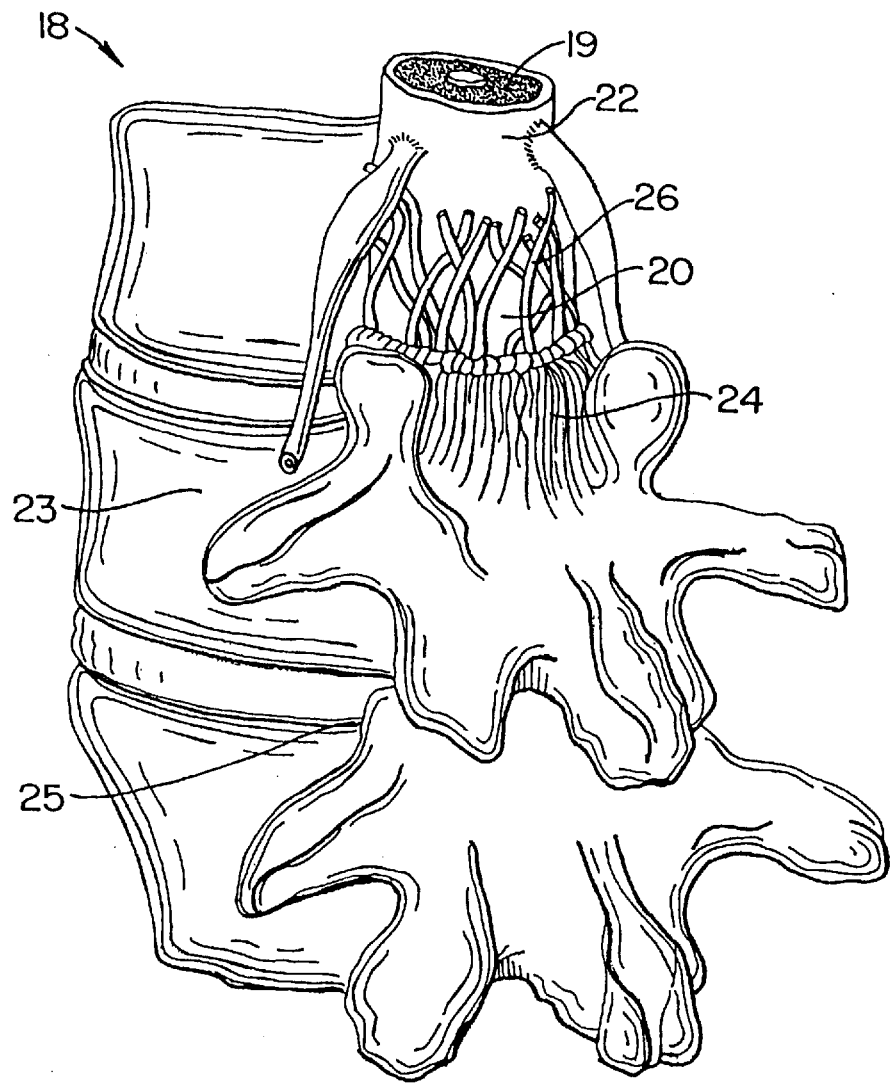
FIG. 2 is a fragmentary view of a spinal column illustrating the position of the epidural space therein.

In the back region or posterior end of the human body, as best illustrated in FIGS. 1 and 2, the epidural space 20 is potential space located in and extending the length of the spine 18: As illustrated in the fragmentary view of a spinal region 18 in FIG. 2, the epidural space 20 has a generally cylindrical or crescent type shape and is defined along one edge or side by the dura mater 22 which surrounds the spinal cord 19. The epidural space is further defined along a second edge or side by the periosteum of the bony vertebrae 23 or by the ligamentum-flavum 24 at the vertebral interspaces 25. Along the interior surface of the ligamentum-flavum 24 lies the venus plexus 26, a complex configuration of veins. The epidural space 20 is a collapsible potential space that contains fat, connective tissue, blood vessels, lymphatic vessels, nerve fibers, and other structures. Various lesions, cystical masses, and nerve damage can occur in and around the epidural space which causes various back problems for the human body. For example, fibrosis ranging from soft to tougher scar tissue may form randomly or in layers and adhere to the dura mater 22 and the periosteum of the body vertebrae 20 or the ligamentum-flavum 24 which form lesions extending across the epidural space 20. These lesions can be caused by post operative scarring of nerves such as from laminectomy procedures. A ruptured, leaking, or torn disk can also cause lesions which are often the source of back pain.

The method of epidural surgery according to the present invention improves visibility in the epidural space 20, of a patient for more effectively conducting therapeutic surgery in and around the epidural space 20 such as applying a steroic fluid, performing a diskectomy, or disrupting a fibrotic lesion. The method of epidural surgery according to the present invention involves distending a portion of the epidural space 20 by filling the portion of the epidural space 20 with a fluid, preferably a liquid such as a normal saline solution, supplied from a catheter 30 positioned in the epidural space 20. As best shown in FIGS. 3–6, a portion of an optical scope 60 is positioned in the distended portion of the epidural space 20 by inserting the optical scope 60 through the catheter 30 to thereby provide a visual image 100 of the epidural space 20.

Figures 5, 6:
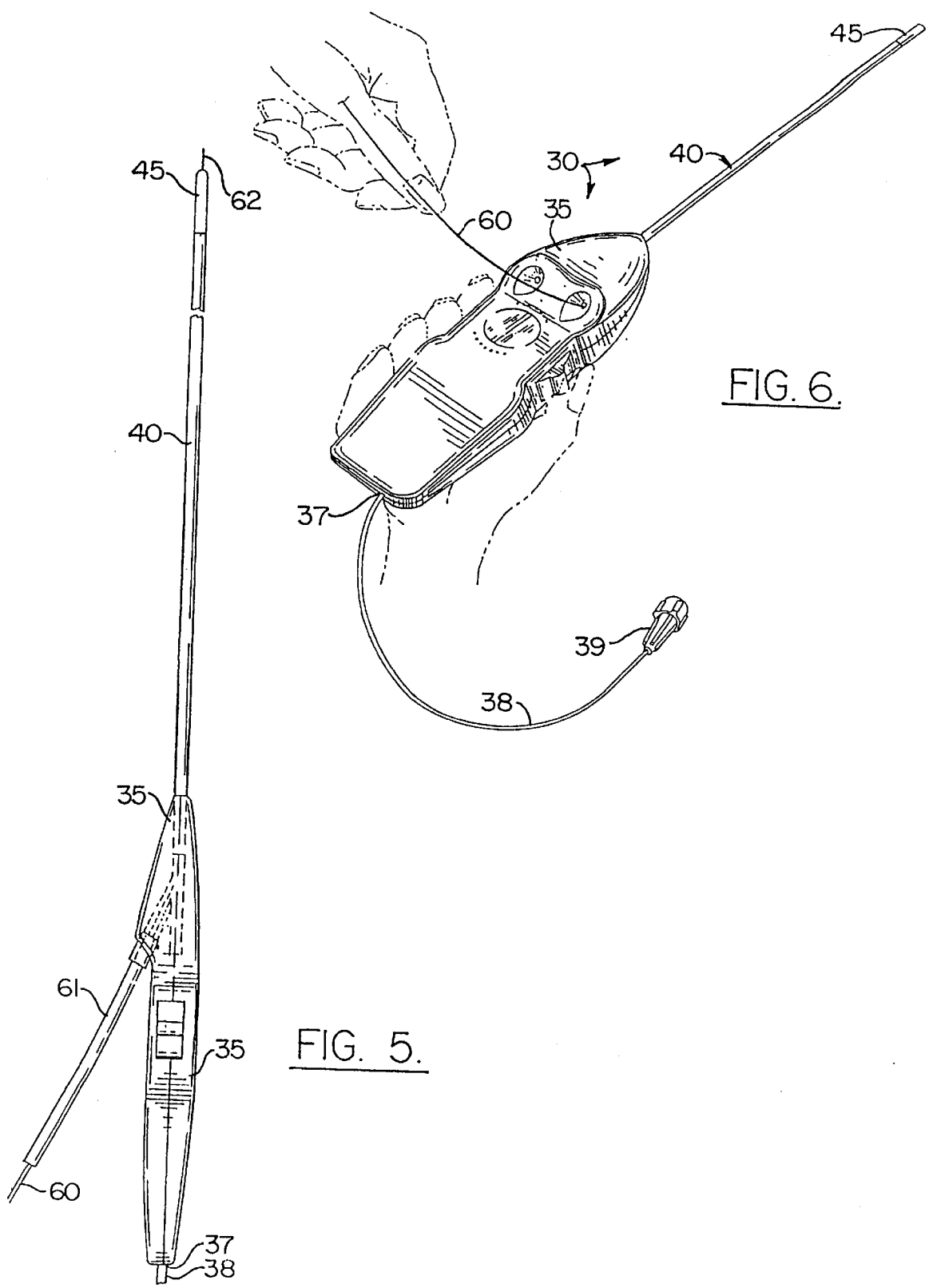
FIG. 5 is a side elevational view of a catheter having a fiberscope inserted therein for the methods according to the present invention.
FIG. 6 is a perspective view of a catheter having a fiberscope inserted therein for the methods according to the present invention.

According to first and second embodiments of the present invention, the catheter 30 may be one of the numerous types of catheters known to those skilled in the art, but preferably is a multi-lumen, steerable catheter 30 as best illustrated with reference to FIGS. 5–12. The multi-lumen, steerable catheter 30 preferably has a multiple durometer tube portion 40 extending outwardly from a handle portion 35 such as disclosed and described in copending U.S. patent applications Ser. No. 07/908,403 filed on Jul. 6, 1992 and Ser. No. 07/970,490 filed on Nov. 2, 1992 which are hereby incorporated herein by reference. The optical scope 60 is preferably an 0.88 millimeter (mm) fiberscope, known to those skilled in the art, that may be inserted through a lumen 41 of the steerable catheter 30, and preferably through a fiberoptic sheath 61 as shown in FIG. 5 and have a portion 62 thereof extend into the epidural space 20. The fiberscope 60 preferably communicates with an imaging apparatus such as disclosed and described in copending U.S. patent application Ser. No. 07/963,431 filed on Oct. 12, 1992 which is also hereby incorporated herein by reference. As such, further details of the steerable catheter 30, the optical scope 60, and the imaging apparatus 80 will not be discussed except in relation to the operation thereof for the methods of epidural surgery according to the present invention.

Figure 3:
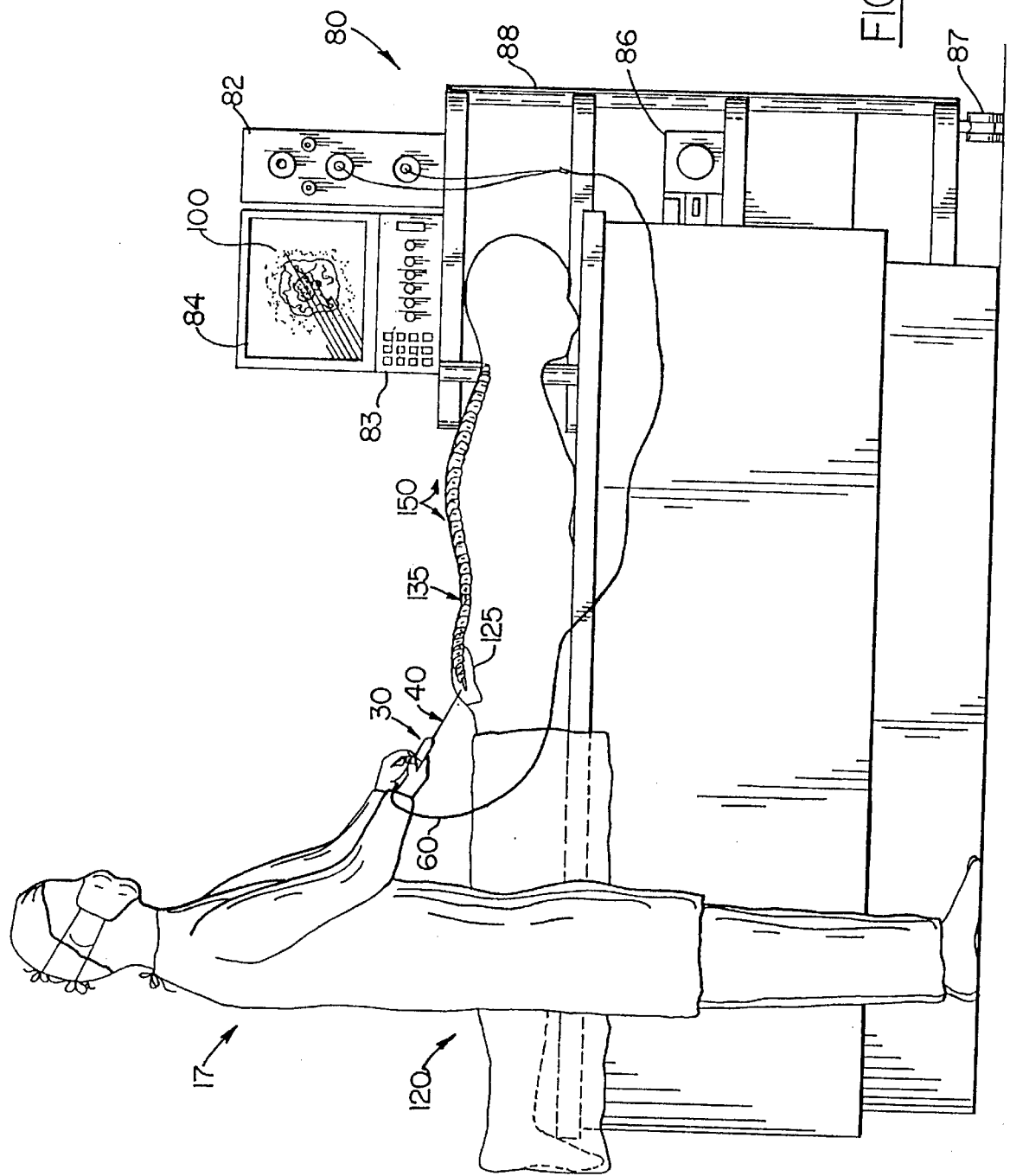
FIG. 3 is an elevational plan view of a surgical operation on a patient having a catheter positioned through an opening in the sacrum region and into the epidural space by a physician for therapeutic treatment of a problem area according to a first embodiment of the present invention.
Figure 7:
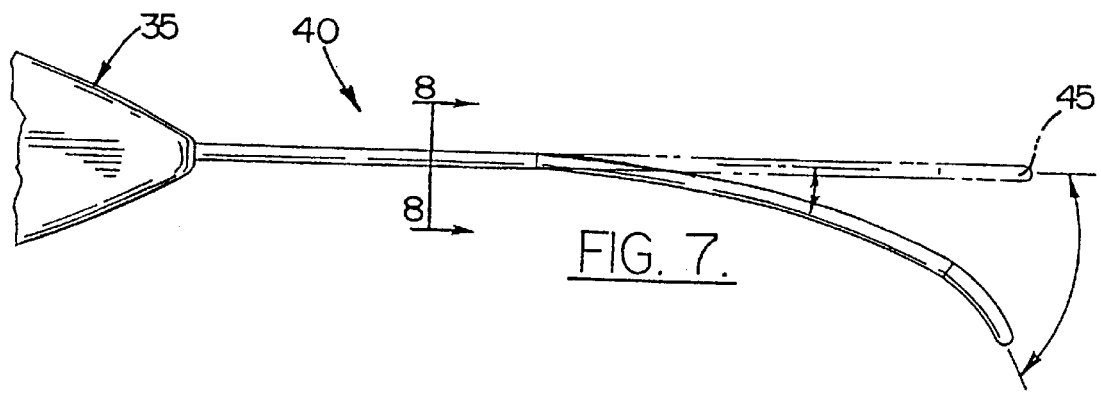
FIG. 7 is fragmentary top elevational view of a catheter for the methods according to the present invention.
Figure 8:
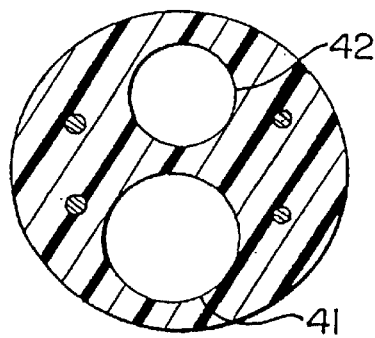
FIG. 8 is an enlarged cross-sectional view of a first embodiment of a catheter taken along line 8—8 of FIG. 7 for the methods according to the present invention.
Figure 9:
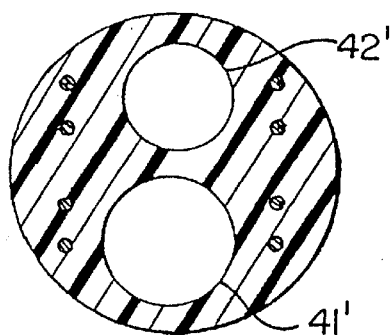
FIG. 9 is an enlarged cross-sectional view of a second embodiment of a catheter taken along line 8—8 of FIG. 7 for the methods according to the present invention.
Figure 10:
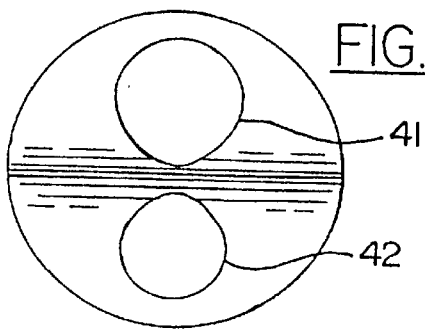
FIG. 10 is an enlarged distal end plan view of a catheter taken from a distal end thereof for the methods according to the present invention.
Figure 11:
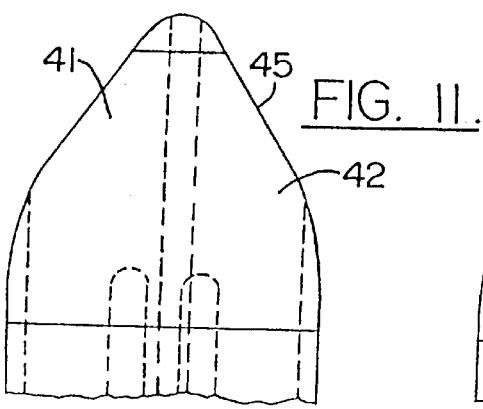
FIG. 11 is enlarged fragmentary top plan view of a distal end of a catheter and having phantom lines therein illustrating the positioning of the multiple lumens within the catheter for the methods according to the present invention.
Figure 12:
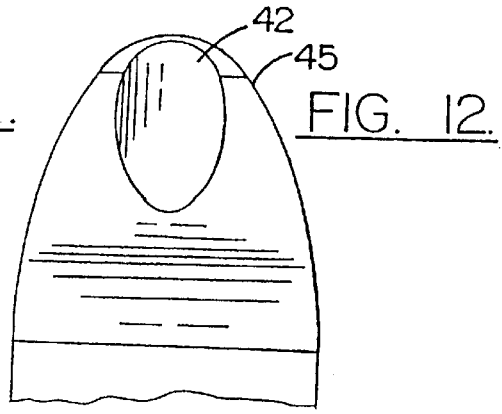
FIG. 12 is enlarged fragmentary side plan view of a distal end of a catheter for the methods according to the present invention.

By providing the combination of the steerable catheter 30, the fiberscope 60, and the imaging apparatus 80, as illustrated in the elevational plan view of FIG. 3, a physician 17, or other medical personnel, can control and manipulate the catheter 30 and the imaging source 82 of the imaging apparatus 80 while simultaneously using surgical tools, such as cutting instruments or the like, and fluids needed for medical operations to thereby allow the physician to positionally locate, isolate, and view problem areas on a television monitor 84, i.e., cathode ray tube display device, within the epidural space 20. The imaging apparatus 80 enables the physician to not only observe the visual image 100 of the distended portion of the epidural space 20, but also provides a means for recording and documenting the problem area such as the video cassette recording 86 mounted below the imaging source 82 and television monitor 84 on the portable stand 88. Since the steerable catheter 30 is preferably quite flexible and maneuverable within the epidural space 20, as best shown in FIGS. 6 and 7, the method also provides less radical interspinal surgical operations because problem areas can more effectively be observed and accessed with the optical scope 60 and steerable catheter 30 combination. Because the imaging apparatus 80 is mounted on a stand 88 having wheels 87, as best shown in FIGS. 5, the physician 17, and other medical personnel, can position the apparatus 80 close to the operation site. The control panel 83 and imaging source 82 of the imaging apparatus 80 provides image 100 adjustments, focus, and magnification to assist in viewing the epidural space 20 and the problem area when the portion of the epidural space 20 is distended by the liquid. It will be understood that the distended portion of the epidural space 20 to be viewed is preferably an amount of the epidural space 20 less than the entire boundaries thereof, the boundaries or peripheries being previously defined and described with reference to FIG. 3.

Figure 13:
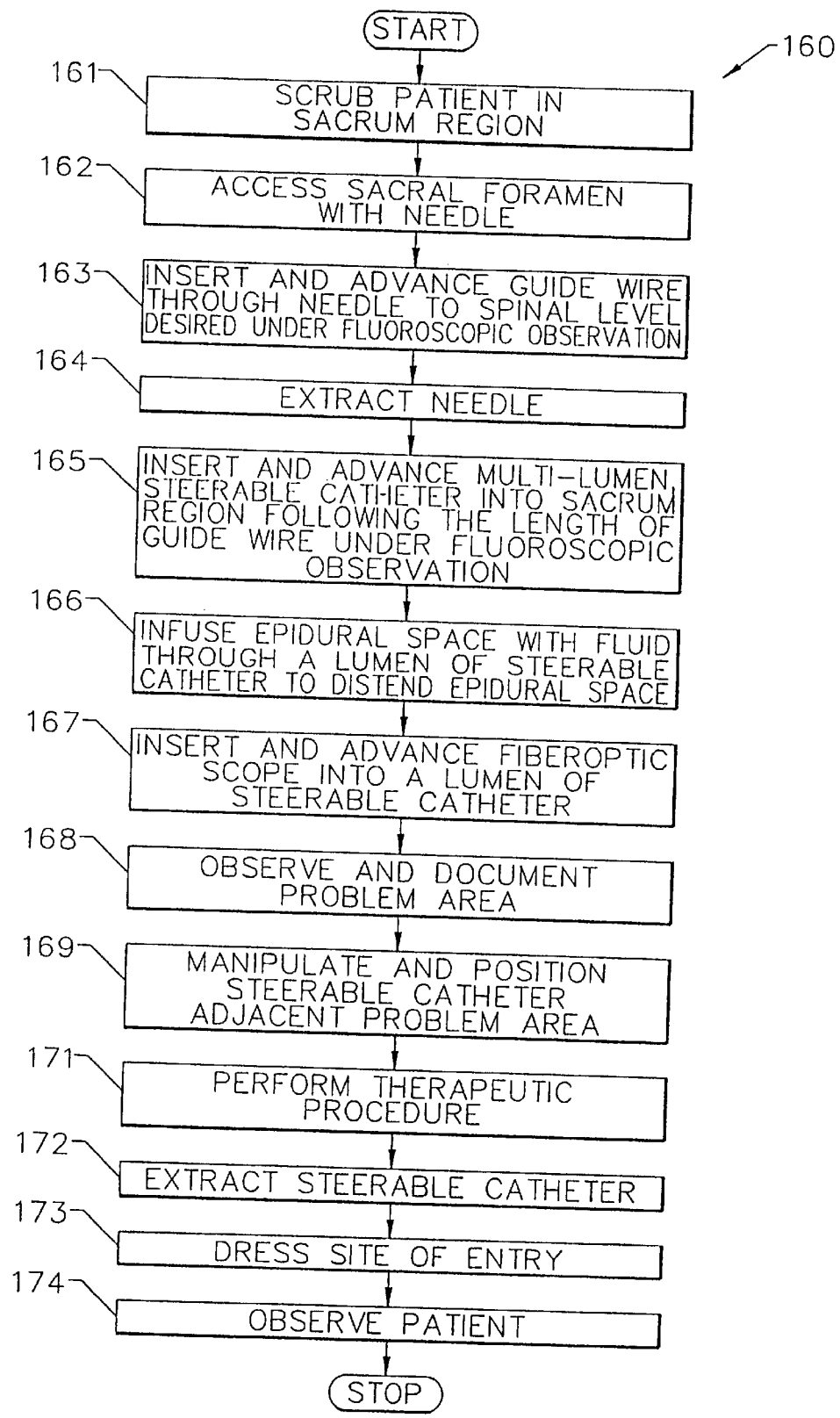
FIG. 13 is a block diagram of a method of epidural surgery according to a first embodiment of the present invention.
Figure 14:
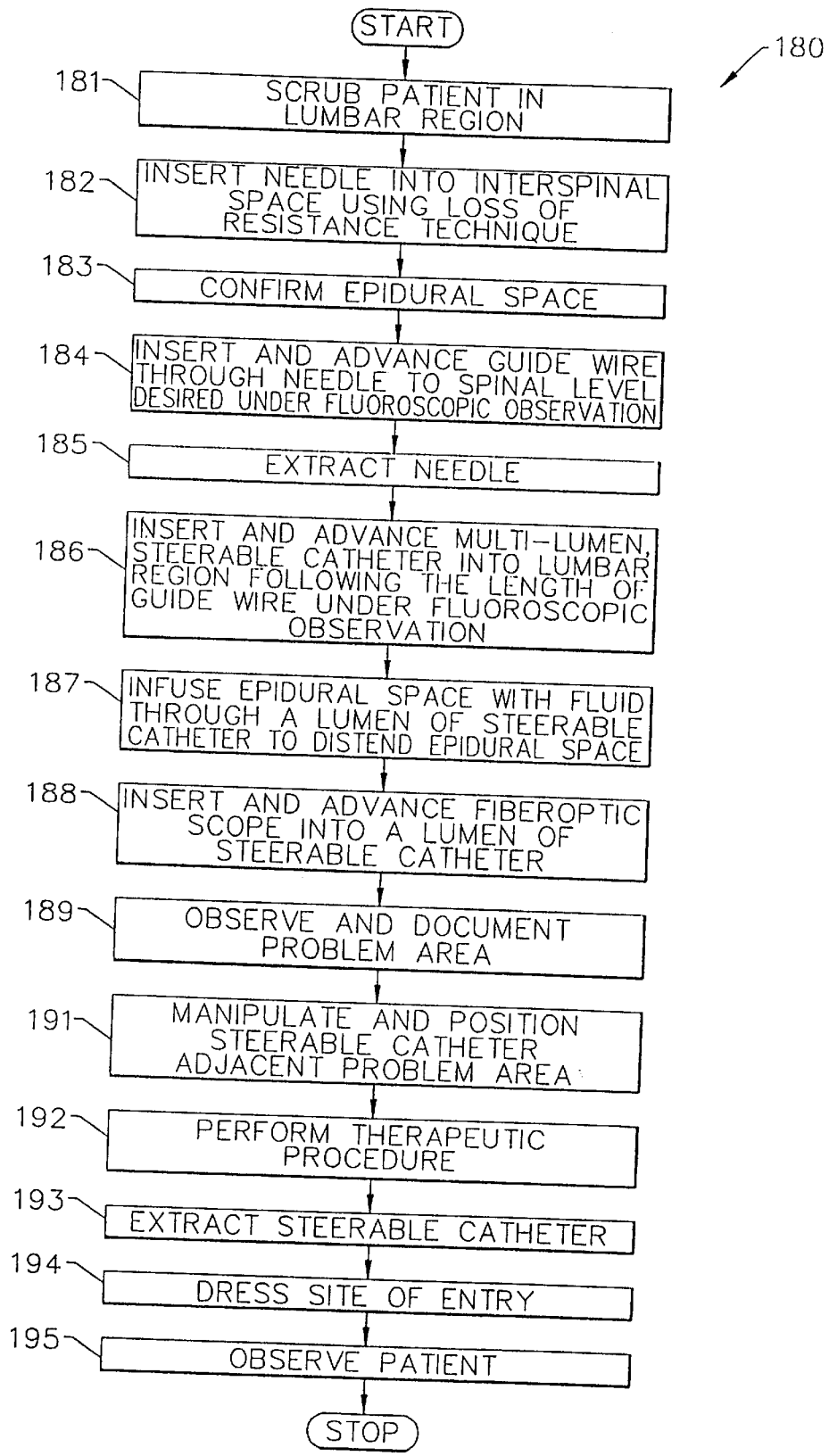
FIG. 14 is a block diagram of a method of epidural surgery according to a second embodiment of the present invention.

More particularly with reference to the block diagrams illustrated in FIGS. 13 and 14, and the elevational plan view of a surgical operation in FIG. 3, the method of epidural surgery according to the present invention includes inserting a needle through the skin of a patient 120, preferably through a sacrum region 125 (FIG. 13) or a lumbar region 135 (FIG. 14) of the patient 120, and into the epidural space 20 to thereby provide an opening from the skin into the epidural space 20 of the patient 120.

As illustrated in FIG. 1, the sacrum region 125 is at a lower end of the spinal column 18 below L-5 and adjacent the pelvic region 28. The sacrum 125 is a triangular shape bone formed generally by five fused vertebrae, i.e., sacral vertebrae, that are wedged dorsally between the two hip bones of the pelvic region 28 in this region of the human anatomy. It will also be understood by those skilled in the art that the invention is also applicable to various animals for veterinarian epidural procedures. The lumbar region 135 extends from L-1 to L-5 between the sacrum region 125 at a lower end and the thorax region (T-1 to T-12) at an upper end. The thorax region (T-1 to T-12) from an upper part 150 (T-12) lumbar region 135 to neck.

As illustrated in FIG. 13, according to a first embodiment of a method of epidural surgery 160 according to the present invention, the patient is scrubbed in the sacrum region 125, preferably in an area around the sacral canal and up to the level of T-8 (FIG. 1) with wide prep iodine, as shown by block 161. The patient 120 is draped, the physician 17 is scrubbed, and dressed in a sterile gown (FIG. 3). The entry site is prepared and a one percent (1%) Xylocaine solution is injected to create a skin wheel. The patient 120 is then sedated with Versed which is individually titrated to the patient's needs. The patient is also monitored with pulse oximetry, EKG, and a blood pressure monitor 42.

After the patient is scrubbed and prepared, a needle, preferably an 18-gauge Touhy needle, is used to access the sacral foramen, as shown by block 162. The ligamentum-flavum 24 (FIG. 2) is pierced and the needle tip is inserted in the sacral hiatus. Under fluoroscopic guidance, as shown by block 163, a guide wire, preferably a 0.035-inch straight tip floppy guide wire, is inserted and advanced through the needle and into the epidural space. The guide wire is preferably radiopaque and formed of stainless steel with a Teflon coating. The physician 17 then preferably fluoroscopically observes the position of the guide wire in the epidural space 20 and advances the guide wire to a spinal level where a suspected problem area within the epidural space 20 may have originated. As shown by block 164, the needle is extracted from the epidural space 20 and preferably discarded.

The catheter 30, and preferably a multi-lumen, steerable catheter, is then inserted over the guide wire and into the opening to the epidural space 20, as shown by block 165. The guide wire functions as a guidance device as the catheter 30 is advanced into the sacral hiatus. Because the catheter 30 is preferably a steerable catheter, the handle 35 and flexible distal end 45 ease the advancement and positioning of the catheter 30 within and around the epidural space 20. Fluid is supplied, and preferably continuously supplied, to a lumen 42 of the steerable catheter 30 to thereby distend a portion of the epidural space 20. The fluid is preferably a liquid such as a normal saline solution. A normal saline bag can be accessed with an I.V. set and coupled to a three-way stopcock, or valve for fluid regulation. A 20 cubic centimeter (cc) syringe is then coupled to a second port of the three-way stop-cock. An access port to a lumen 42 of the catheter 30 is also preferably coupled to a third port of the stop-cock. The fluid may also enter through tube portion 38 at a proximal end 37 at the handle portion 35 of the catheter 30 (as best shown in FIG. 6). The 20 cc syringe is used first to extract all the air bubbles from the I.V. set and then fill the I.V. set with a normal-saline, liquid solution for distention of the epidural space. Twenty cc's of saline can be infused into the epidural space 20, as shown by block 166. The 20 cc's are sufficient to increase the pressure in a portion of the epidural space 20 and create a cavity in which the nerve root or other structures can be observed. The position of the steerable catheter 30 within the epidural space may also be fluoroscopically observed. The catheter 30, like the guide wire, is also preferably radiopaque. Under such circumstances, the physician can advance the steerable catheter 30 under the fluoroscopical observation to the suspected problem area.

Figure 4:
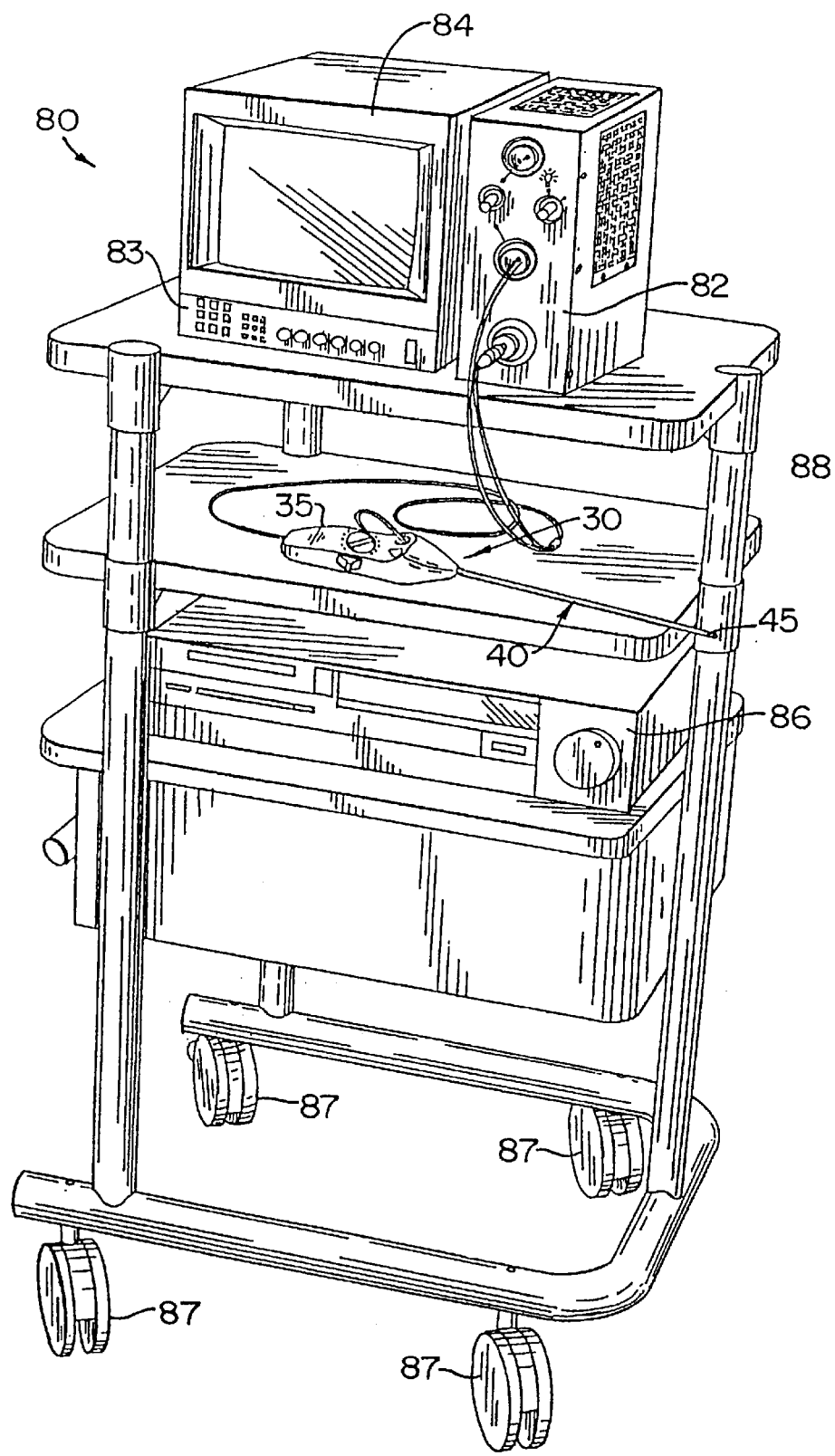
FIG. 4 is perspective view of an imaging apparatus for the methods according to the present invention.

As shown by block 167, an optical scope 60, preferably a fiber optic scope or fiberscope, is then inserted preferably within another lumen 41 of the multi-lumen, steerable catheter 30. The fiberscope 60 can enter an access port in the handle portion 35, as best shown in FIG. 6, or enter at a proximal end 37 of the handle portion 35 as shown in FIG. 3 or 4. It will also be understood that the fiberscope 60 can be inserted prior to the advancement of the catheter 30 in the epidural space 20. A portion of the optical scope 60 is advanced within the lumen 41 of the steerable catheter 30 and into the distended portion of the epidural space 20. The optical scope 60 preferably is not radiopaque and preferably will not extend into the epidural space 20 more than about one centimeter (cm). With the fluid distending a portion of the epidural space 20, the optical scope 60 can also be positioned within the distal tip 45 of catheter 30 and still view the distended portion of the epidural space 20. The optical scope 60 illuminates the distended portion of the epidural space 20 to thereby visualize and display the epidural space 20 and a problem area therein with the imaging apparatus 80, as shown by block 168. The catheter 30 can be manipulated to place the distal end 45 into an optimal position to avoid any adhesions or naturally occurring fat globules that could hinder the flow of drugs such as a steroic fluid or that could hinder positioning of instruments or devices used in surgical procedures. As shown by block 169, the catheter 30 is manipulated until the problem area such as an inflammation is recognized by its redness, increased vascularity, or other systems. The problem area is then observed and documented. As shown by block 171, a treatment is then performed to the problem area within the epidural space such as the applying of a steroic fluid to a nerve area, disrupting a fibrotic lesion, performing a diskectomy, or other types of procedures. These therapeutic treatments preferably include positioning a distal end 45 of the steerable catheter 30 adjacent the problem area within the epidural space 20 and treating the problem area within the epidural space 20 through a lumen 41 or 42 of the steerable catheter 30.

After performing the treatment, the catheter 30 is then slowly extracted and a dressing is placed at the site of entry, as shown by blocks 172, 173. The patient is observed, preferably for about two hours, then discharged, as shown by block 174. The patient's chart is completed and a one week follow-up appointment may be made.

As illustrated in FIG. 14, according to a second embodiment 180 of a method of epidural surgery of the present invention, a lumbar region 135 of the patient 120 is scrubbed and prepped, preferably in and around the L3–L4 area (FIG. 1), as shown by block 181. In this second embodiment, in contrast to the first embodiment as illustrated in FIG. 2, the patient 120 is preferably in a sitting position to spread the L1–L5 vertebrae to make access easier. It will also be understood that other sites of entry along the spinal column 18, besides the sacrum or caudal region 125 and lumbar region 135 of the patient 120, may be performed according to the present invention.

As shown by block 182, an 18-gauge Touhy needle is inserted into the interspinal space, such as between L3 and L4, using the loss of resistance technique well known to those skilled in the art. The epidural space 20 is confirmed and a guide wire, preferably a 0.035-inch straight floppy top guide wire, is inserted and advanced through the needle to the spinal level where the suspected problem area may be located in and around the epidural space 20, as shown by blocks 185, 186. The needle is then extracted (block 185) and preferably discarded.

As shown by block 187, the catheter 30 is inserted and advanced over the guide wire to the suspected problem area. The epidural space 20 is then infused with a fluid, as previously described with reference to the first embodiment, and distended (block 187). A portion of the optical scope 60 is inserted and advanced through a lumen 41 of the catheter 30 and into the distended portion of the epidural space 20, as shown by block 188. The problem area is observed and documented, and the catheter is manipulated and positioned adjacent the problem area for more effectively performing a therapeutic procedure, such as previously described (blocks 189, 191). A therapeutic procedure is then performed, also as previously described, as shown by block 192. The catheter 30 is then slowly extracted, the entry site is dressed, and the patient is observed (blocks 193–195). A follow-up visit is then scheduled and the patient discharged.

The method of the present invention thereby provides improved visualization of the epidural space and more effective treatment of problems areas therein. The method allows the physician to effectively observe and document the problem area and then determine the most effective treatment for the patient. Since the steerable catheter is preferably quite flexible and maneuverable within the epidural space, the method also provides less radical interspinal surgical operations because problem areas can more effectively be observed and accessed with the optical scope and steerable catheter combination.

In the drawings and specification, there have been disclosed typical preferred embodiments of the invention and, although specific terms are employed, they are used in a generic and descriptive sense only and not for the purposes of limitation. The invention has been described in considerable detail with specific reference to various embodiments. It will be apparent, however, that various modifications and changes can be made within the spirit and scope of the invention as described in the foregoing specification and defined in the following appended claims.

That which is claimed is:

1. A method of epidural surgery comprising the steps of:
   distending a portion of the epidural space of a patient by providing the portion of the epidural space with a fluid supplied from a catheter positioned in the epidural space to thereby improve visual imaging of the epidural space.

2. A method of epidural surgery according to claim 1, further comprising the step of performing a therapeutic treatment on a problem area within the distended portion of the epidural space.

* * * * *

UNITED STATES PATENT AND TRADEMARK OFFICE
CERTIFICATE OF CORRECTION

PATENT NO. : 5,857,996
DATED : January 12, 1999
INVENTOR(S) : Phillip Jack Snoke It is certified that error appears in the above-identified patent and that said Letters Patent is hereby corrected as shown below:

On the title page,

| [54] Title: | Strike: | "EPIDERMAL" |
| | Insert: | -- EPIDURAL -- |

| Column 1: Title | Strike: | "EPIDERMAL" |
| | Insert: | -- EPIDURAL -- |

Signed and Sealed this

Eighteenth Day of May, 1999

Attest:

Q. TODD DICKINSON

*Attesting Officer*   *Acting Commissioner of Patents and Trademarks*